United States Patent [19]

Markowitz

[11] Patent Number: 5,312,450
[45] Date of Patent: May 17, 1994

[54] PACEMAKER FOR TERMINATING PACEMAKER-MEDIATED TACHYCARDIA
[75] Inventor: H. Toby Markowitz, Roseville, Minn.
[73] Assignee: Medtronic, Inc., Minneapolis, Minn.
[21] Appl. No.: 877,575
[22] Filed: May 1, 1992
[51] Int. Cl.⁵ .............................................. A61N 1/00
[52] U.S. Cl. ...................................................... 607/14
[58] Field of Search .................... 128/419 PG, 419 PT

[56] References Cited
U.S. PATENT DOCUMENTS

| | | | |
|---|---|---|---|
| 4,312,355 | 1/1982 | Funke | 128/419 |
| 4,401,119 | 8/1983 | Herpers | 128/419 |
| 4,428,378 | 1/1984 | Anderson et al. | 128/419 |
| 4,539,991 | 9/1985 | Boute et al. | 128/419 |
| 4,554,920 | 11/1985 | Baker, Jr. et al. | 128/419 |
| 4,569,350 | 2/1986 | Mumford et al. | 128/419 PT |
| 4,686,989 | 8/1987 | Smyth et al. | 128/419 PT |
| 4,712,556 | 12/1987 | Baker, Jr. | 128/419 |
| 4,788,980 | 12/1988 | Mann et al. | 128/419 |
| 4,951,667 | 8/1990 | Markowitz et al. | 128/419 |
| 5,074,308 | 12/1991 | Sholder et al. | 128/419 PT |

OTHER PUBLICATIONS

Chalfee, Richard V., "Pacemaker-Mediated Tachycardia: Engineering Solutions", PACE, vol. 11, Nov. 1988, Part II, pp. 1917-1928.
Duncan et al., "Prevention and Termination of Pacemaker-Mediated Tachycardia in a New DDD Pacing System (Siemens-Pacesetter Model 2010T)", PACE, vol. 11, Nov. 1988, pp. 1679-1683.
Jordaens et al., "The Prevention of Pacemaker Mediated Tachycardias in Double-Chamber Pacing", ACTA CARDIOLOGICA, vol. XXXIX, 1984, 6, pp. 449-462.
LaMaison et al., "A New Algorighm for a High Level of Protection Against Pacemaker-Mediated Tachycardia", PACE, vol. 11, Nov. 1988, Part II, pp. 1715-1721.

Primary Examiner—Lee S. Cohen
Assistant Examiner—Marianne Parker
Attorney, Agent, or Firm—Harold P. Patton; Gregory P. Gadson

[57] ABSTRACT

In order to terminate pacemaker-mediated tachycardia (PMT), a pacemaker (or "Pacer") capable of atrial synchronized ventricular pacing, defines a retrograde sensing window after a ventricular paced event. If a preset number of sequential retrograde sensed events occur within this window in consecutive pacing cycles the post ventricular atrial refractory period (PVARP) is extended for one pacing cycle (EXT PVARP) and the pacer will not attempt to interrupt a PMT for a relatively long preset interval thereafter.

17 Claims, 4 Drawing Sheets

PACEMAKER FOR TERMINATING PACEMAKER-MEDIATED TACHYCARDIA

BACKGROUND OF THE INVENTION

1. Field of the Invention

The present invention relates to atrial synchronized ventricular pacemakers which can generate ventricular pacing events in response to sensed atrial events. More particularly, the invention relates to a pacer which modifies its operation to terminate pacemaker-mediated tachycardia.

2. Description of the Prior Art

Atrial synchronized ventricular inhibited pacing modes have been widely adopted for pacing therapy. The principal atrial synchronized operating mode is referred to as "DDD". This mode has a sensor augmented variant mode called "DDDR".

A DDD pacemaker includes an atrial sense amplifier to detect atrial depolarizations of the heart. If, after an appropriate delay, the ventricle of the heart fails to beat, the pacemaker supplies a ventricular pacing stimulus to the ventricle through an appropriate lead system. Pacemakers which perform this function have the capability of tracking the patient's natural sinus rhythm and preserving the hemodynamic contribution of the atrial contraction over a wide range of heart rates.

The principal problem associated with atrial tracking pacing modalities is referred to in the industry as "PMT" for Pacemaker-Mediated Tachycardia. In many patients, a ventricular stimulus may result in retrograde conduction from the ventricle to the atrium. If retrograde conduction reaches the atrium while the atrial tissue is refractory, the atrium does not depolarize, and no PMT occurs.

However, if the atrial tissue is not refractory, the retrograde conduction can stimulate a "beat" of the atrial tissue which may be detected by the pacemaker's atrial sense amplifier. Consequently, the pacemaker synchronizes to the retrograde "beat" and paces the ventricle again, after an AV delay interval. In this instance, the atrial sense amplifier is not detecting natural sinus depolarizations of the atria, but rather it is detecting atrial depolarizations caused by retrograde conduction. Consequently, the pacer is no longer following a natural atrial rhythm, but rather the pacing rate is determined by the retrograde conduction time of the patient and the AV delay interval of the pacer. This process results in ventricular pacing at an inappropriate rate which is at or below the upper ventricular rate limit of the pacer, and an inappropriate atrio-ventricular sequence.

A variety of events may initiate PMT, including: the occurrence of premature ventricular contractions (PVC's); pacer Wenkebach prolongation of AV interval; loss of atrial capture; atrial sensing of noise, and long programmed AV intervals.

Many approaches have been adopted to address the PMT problem including the techniques taught by:

U.S. Pat. No. 4,788,980 to Mann et.al., which teaches a retrograde sense period, invoked by the detection of a premature ventricular contraction (PVC). An atrial event detected in this window results in the generation of an atrial paced event if no intervening atrial or ventricular event is sensed. This patent teaches the suspension of the pacemaker's maximum tracking interval (MTI) after the detection of a PVC. This patent also teaches the shortening of the AV interval in response to the detection of a PVC.

U.S. Pat. No. 4,539,991 to Boute, teaches a pacemaker which monitors the atrial rate, then examines the stability of the VA conduction time to ascertain whether the pacer is participating in a pacemaker-mediated tachycardia at the ventricular rate limit.

U.S. Pat. No. 4,401,119 to Herpers, discloses a pacemaker which avoids PMT by extending the atrial refractory period upon the detection of a PVC.

U.S. Pat. No. 4,554,920 to Baker, et al., teaches a pacemaker which avoids PMT by extending the atrial Refractory period upon the occurrence of specific events, such as a PVC, noise reversion, or a programmed mode change.

U.S. Pat. No. 4,712,556 to Baker, teaches a pacemaker which inhibits a ventricular paced event after a predefined number of successive ventricular paced events have occurred at the ventricular rate limit.

SUMMARY OF THE INVENTION

In the present invention, a retrograde sense window is established after a ventricular paced event. If an atrial sensed event occurs within this sensing window, a retrograde sensed event counter is incremented by one count. When a defined number has been reached by the retrograde sensed event counter, the pacemaker extends the post ventricular atrial refractory period (PVARP) to a fixed amount for one pacing cycle. This is called PVARP extension. Once an extended PVARP has begun, the pacemaker does not count retrograde sensed events nor extend PVARP again for a period of time referred to as the "disable interval". The starting and stopping times of these intervals may be varied. However, it is preferred to start the retrograde sense window At the conclusion of the programmed or sensor-varied post ventricular atrial refractory period. It is preferred to define a PVARP limit interval extending from the preceding VP event for a fixed time such as 400 milliseconds. The retrograde sense window is defined as the difference between these two intervals. Thus, the retrograde sense window extends from the conclusion of programmed or sensor-varied PVARP to the conclusion of the PVARP limit interval. Similarly, it is preferred that the extended PVARP begins at the end of the programmed or sensor-varied PVARP interval and ends at the conclusion of the PVARP limit interval. It is also preferred to start the retrograde sense window "disable interval" coincident with the delivery of a ventricular paced event, and to have this interval extend for a fixed duration of approximately 90 seconds. The preferred number of consecutive sensed events required to invoke the extended PVARP is eight.

The purpose of the retrograde sense window is to record atrial sensed events which occur in close proximity to a preceding ventricular paced event since these events may be due to retrograde conduction. The purpose of the occurrence of the extended PVARP is to end synchronization to retrograde sensed events. The purpose of the retrograde sense window disable interval is to limit the frequency at which the pacemaker or pacer attempts to interrupt a PMT by use of the extended PVARP. The particular time durations of the retrograde sense window, extended PVARP, and the disable interval should be selected with these objectives in mind.

It should be noted that neither the duration nor the exact starting time for the disable interval is critical to the operation of the pacer, and other criteria can be used to set the duration of the "disable interval", including counting a suitable number of sensed cardiac events such as 60 consecutive ventricular sensed or paced events. Similarly, the number of consecutive sensed events within the retrograde sense window can be made a physician-programmable variable as well.

BRIEF DESCRIPTION OF THE DRAWING

In the various figures of the drawing, like reference numerals indicate identical structures throughout the several views, wherein.

DETAILED DESCRIPTION OF THE PREFERRED EMBODIMENT

The present invention may be incorporated into pacers which pace the ventricle in response to detected atrial events. For example, the DDD type of pacer taught by U.S. Pat. No. 4,312,355 to Funke, hereby incorporated by reference, is an appropriate candidate pacer for the inclusion of present invention. Another rate responsive pacer suitable for use with the invention is taught in U.S. Pat. No. 4,951,667 to Markowitz et.al., hereby incorporated by reference, which teaches a dual chamber, activity based rate responsive pacer of the DDDR type. This pacer utilized sensed patient activity to set the pacer's "sensor" rate.

Figure 1:
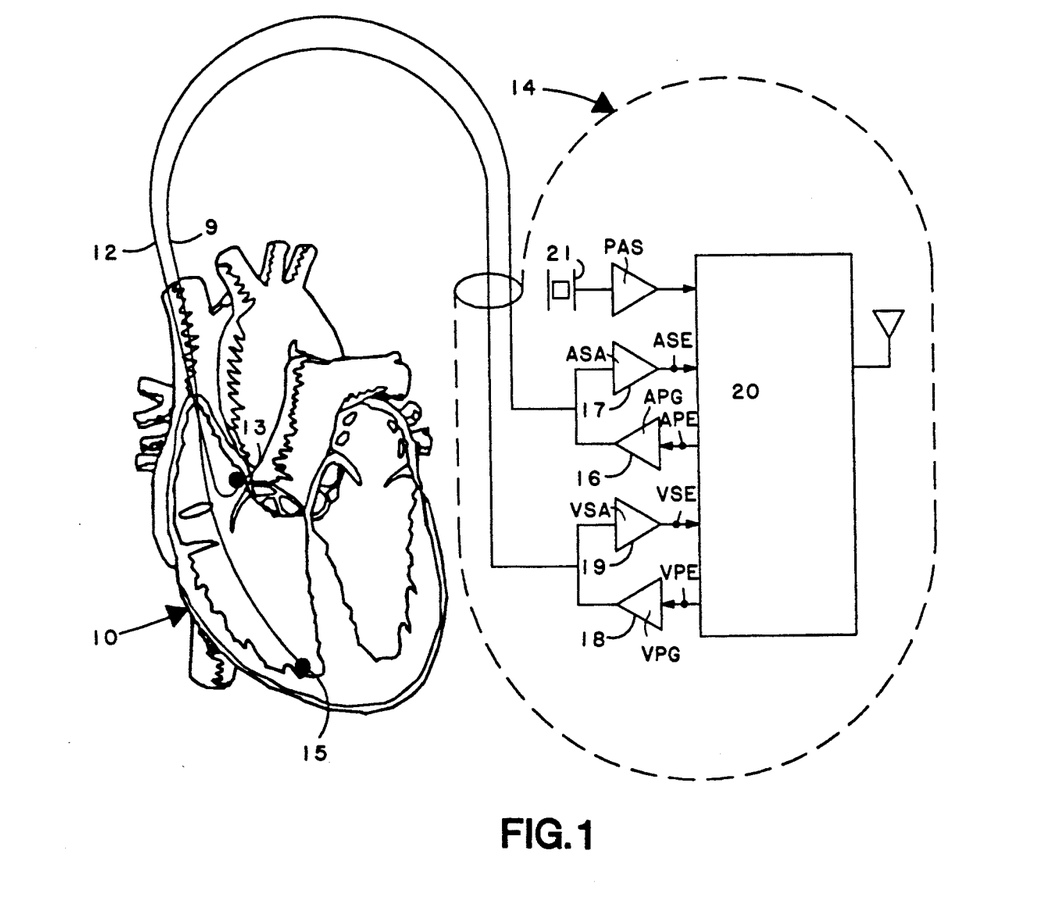
FIG. 1 is block level diagram of a DDDR pacer, illustrative of the invention.

FIG. 1 is block level diagram which sets forth the structures required to incorporate the invention into a DDD/DDDR pacer. In the drawing the patient's heart 10 has an atrial pacing lead 12 passed into the right atrium and a ventricular lead 9 passed into the right ventricle. The atrial lead 12 has an atrial electrode array 13 which couples the pacer 14 to the atrium. The ventricular lead 9 has a ventricular electrode array 15 for coupling the pacer 14 to the ventricular tissue of a patient's heart 10.

The atrial electrode array 13 is coupled to both an atrial pace stimulus generator 16 (APG), and an atrial sense amplifier 17 (ASA). In a similar fashion, the ventricular electrode array 15 is coupled to a ventricular pace stimulus generator 18 (VPG) and a ventricular sense amplifier 19 (VSA).

FIG. 1 shows a preferred patient activity sensor (PAS) 21 and appropriate signal conditioning circuitry which can be provided to alter the pacer operation in response to the sensed motion of the patient. An appropriate activity based rate responsive system is taught by U.S. Pat. No. 4,428,378 to Anderson et al., which is incorporated by reference herein. It should be appreciated that alternate sensors can be provided to achieve rate and PVARP variation based upon other sensed physical parameters.

In general the atrial sense amplifier ASA 17 detects depolarizations of atrial tissue and generates an atrial sensed event ASE to indicate the detection of an atrial beat of the patient's heart. Similarly the ventricular sense amplifier VSA 19 responds to a ventricular beat of the patient's heart and generates a corresponding ventricular sensed event VSE.

The pacer logic 20 is coupled to the sense amplifiers and the logic generates various time intervals in response to detected atrial and ventricular sensed events and generates both atrial paced event and ventricular paced event signals in response to timer logic and the sense amplifier signals. The principal timing functions are set forth in Table 1, below.

TABLE 1

| Timer | Timing Functions Starting Event(s) | Ending Event(s) |
|---|---|---|
| PPVARP | VPE or VSE | Timeout |
| V-A (DDDR) or V-A (DDD) | VSE or VPE | APE |
| URL | VSE or VPE | Timeout |
| AVD | APE or ASE | VPE or VSE |
| RLI | VSE or VPE | Timeout |
| Disable Interval (T) | VPE | Timeout |

For example, timer logic 20 is provided with means to time out a programmed AV delay period (AVD). The AV delay period is initiated by the occurrence of either an atrial sensed or atrial paced event. The AV delay period may end with the generation of a ventricular paced event (VPE).

Logic 20 also provides for a programmed post ventricular atrial refractory period (PPVARP). The PPVARP period begins with either a ventricular paced event (VPE) or a ventricular sensed event (VSE) and expires at the conclusion of a physician-set time interval, or may be adapted from the sensor signal (sensor rate).

The logic also times out a refractory limit interval (RLI) which begins with the occurrence of a ventricular paced event. Pacer logic 20 also times out a disable interval period of a fixed but physician-selected duration. This disable interval time period begins upon the occurrence of a ventricular paced event (VPE) in a pacer cycle where the next post ventricular atrial refractory period is extended. Pacer logic 20 times out an upper rate limit interval (URL). This timer is initiated by the occurrence of a ventricular paced event (VPE) or ventricular sensed event (VSE) and limits the upper rate at which ventricular stimuli are delivered to the heart. Preferably two separate lower rate interval timer functions are provided. The first is set by the physician when the base pacing rate is selected. This DDD VA time interval extends from the occurrence of a ventricular sensed event (VSE) or ventricular paced event (VPE) and it may end with the generation of an atrial paced event (APE). The duration of the second lower rate time interval is a function of the measured patient activity acquired by the activity sensor 21. Typically, this DDDR VA time interval begins with a sensed or paced ventricular event (VSE or VPE, respectively) and has a time duration reflecting patient activity. In this art such structures are well known, and a variety of techniques can be used to implement the required timer functions.

The pacer logic 20 is also coupled to the paced event pulse generators. For example, atrial paced event signals are coupled to the atrial pace stimulus generator 16 to produce an atrial pacing stimulus while the ventricular paced event signal generates a ventricular pacing stimulus through the ventricular pace stimulus pulse generator 18.

Figure 2:
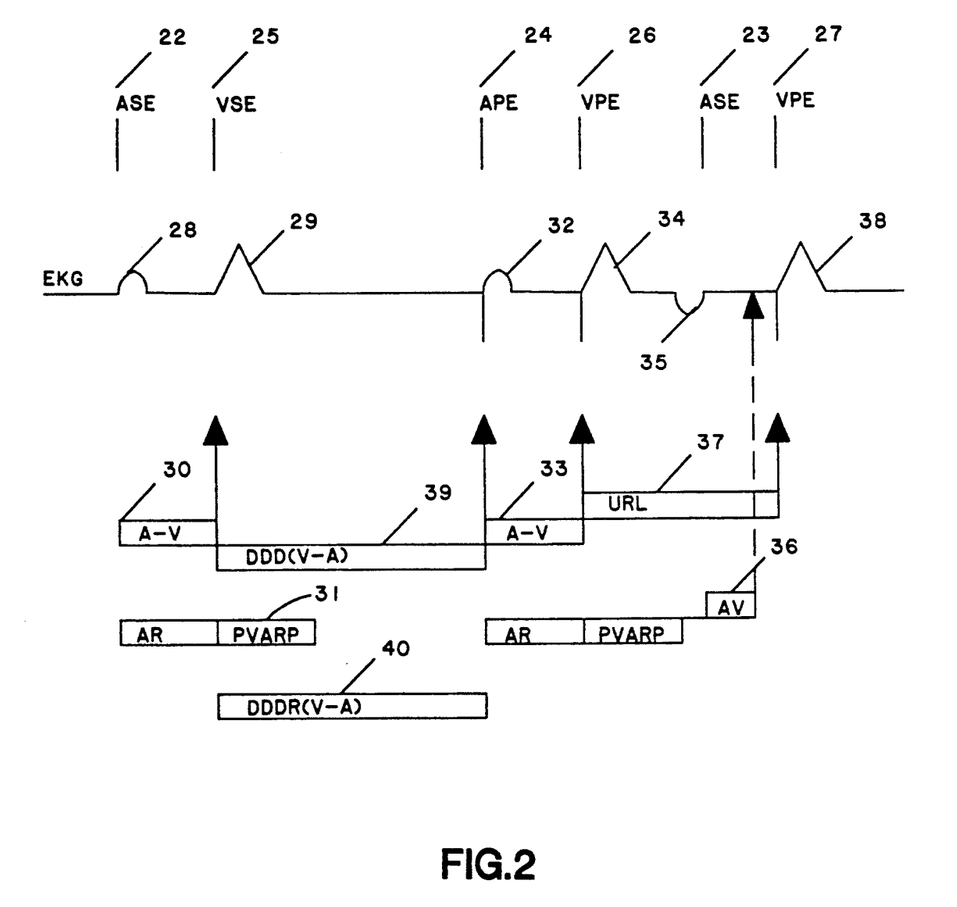
FIG. 2 is a timing diagram depicting the initiation of a PMT in a DDD/DDDR pacer.

FIG. 2 is a timing diagram which depicts a sequence of operation of the pacer of FIG. 1. In the drawing the pacer logic 20 responds to the atrial depolarization or P-wave 28 and generates the atrial sensed event (ASE) 22. An atrial refractory period (ARP) 48 starts after the beginning of the P-wave 28. The ASE 22 starts the AV delay timer within logic 20 giving rise to the AV delay interval 30 shown on the drawing..Prior to the expiration of the AV delay interval 30, and at the end of the atrial refractory period (ARP) 48, the ventricle of the heart depolarizes as indicated by R-wave 29. The corresponding ventricular sensed event VSE 25 starts the programmed or sensor varied post ventricular atrial refractory period 31, abbreviated "PPVARP" throughout. The detected ventricular sensed event 25 also starts the pacers VA timer functions 39 and 40 within logic 20.

Traditionally the VA time period 39 is selected indirectly when the physician sets a lower R—R rate interval or A—A rate interval and an AV delay. As shown in the figure, sensor data can be used to set an alternative VA interval 40. Typically, the pacer logic generates an APE upon the first to expire of the two VA time intervals. In the sequence depicted the first to expire timer is the DDD mode VA timer 39, rather than the sensor varied-timer 40. In the drawing, the pacer logic generates the atrial paced event (APE) 24 since no naturally occurring atrial depolarization occurs within the VA time 39.

Assume in this example that atrial capture has been lost. As a result, a normal stimulated P-wave is not produced in response to the atrial paced event 24. Thus, the point 32 at which a stimulated P-wave would have occurred shows only an atrial pacing spike and no accompanying p-wave. The pacing spike 32 is followed by an atrial refractory period (ARP) 49. The atrial paced event 24 starts the AV delay 33 timer function. In this instance no naturally occurring ventricular depolarization has occurred within the AV delay time 33 and a ventricular paced event 26 signal is generated, resulting in the stimulated R-wave 34. Because of atrial capture loss, the AV node of the heart is non-refractory, permitting retrograde conduction of the stimulated R-wave 34 which gives rise to a retrograde P-wave 35. In response to the P-wave 35, an ASE 23 is generated, which starts an AV delay interval 36. The above illustrates only one example of how retrograde conduction may occur. Some of the other causes of retrograde conduction are mentioned in the "Description of the Prior Art" section supra., while discussing the PMT phenomenon.

Since the retrograde P-wave 35 occurs outside the PPVARP 90 (which begins at the start of the Rewave 34) it initiates the AV delay interval 36 which times out, causing the ventricular paced event 27. The delivery of this stimulus to the ventricle is delayed by the upper rate limit timer function 37 within logic 20 and is delivered to the ventricle at the conclusion of the upper rate limit timer period as indicated by the position of stimulated R-wave 38. This sequence of operation shows how an inappropriate ventricular stimulus 38 can be generated by the detection of the retrograde sensed event 35. If this sequence of events reoccurs then the result is PMT.

Figure 3:
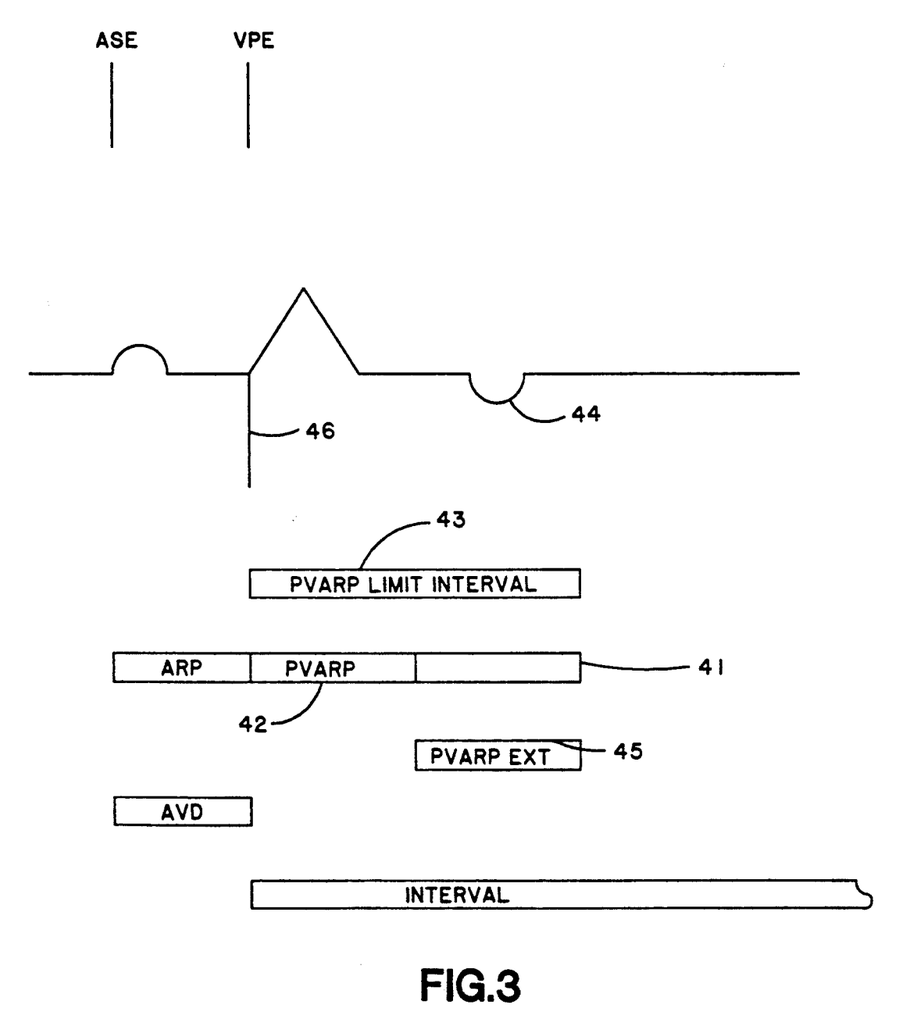
FIG. 3 is a timing diagram depicting the operation of the invention.

FIG. 3 shows a portion of the timing diagram of the pacer and illustrates a preferred implementation of the invention. In FIG. 3, a retrograde atrial sensed event 44 has occurred. In the drawing a refractory limit interval 43 (RLI) is defined extending from the ventricular paced event 46 for 400 ms in the preferred embodiment. A retrograde sensing window 41 is defined as the interval difference between the normal PPVARP 42, and the end of the refractory limit interval 43. An atrial sensed event or a retrograde P-wave such as 44 which occurs within the window is counted in a retrograde sensed event counter established in the logic 20. When, for example, eight consecutive V pace - A sense sequenced events are detected in eight consecutive pacer cycles (with no other intervening events, such as atrial refractory sensed events), the post ventricular atrial refractory period is extended to the end of the refractory limit interval 43, for one pacing cycle, thus establishing an extended PVARP or EXT PVARP 45, during which no ventricular paced events can occur. The refractory limit interval 43 may be fixed or physician programmable. Alternatively, the extended PVARP, EXT PVARP 45, could be of a greater duration than the refractory limit interval 43 to terminate PMT in cases where the retrograde conduction time might vary from beat to beat. It is preferred to require a relatively small fixed number of such atrial sensed events within the window to occur consecutively to invoke the extended refractory period 45. However the number of events can be made a physician adjustable parameter. Once the EXT PVARP interval 45 occurs for one pacing cycle the extension process cannot again occur until a "disable interval" has elapsed, and the retrograde sensed event counter has reached a count of 8 in the preferred embodiment. In the drawing this disable interval 47 is shown starting with the ventricular paced event 46, and extending for a fixed period of time T. As previously described the preferred duration is fixed and set to approximately 90 seconds. In the preferred embodiment the disable interval is implemented by logic which ignores refractory sensed events for 90 seconds. Use of a timed disable interval as opposed to a counted (number of heart cycles) disable interval makes it easier for an observer to diagnose the occurrence of tachycardia without having to actually count a large number of cardiac events.

The pacer 14 does not distinguish between tachycardia of sinus origin and tachycardia due to retrograde conduction (pacemaker-mediated). It is desirable with some patients that a degree of sinus tachycardia be permitted where it is in response to increased physical exertion, for example. It is also desirable to terminate pacemaker-mediated tachycardia, while permitting sinus tachycardia in some patients. The disable-interval 47 of the present invention prevents the termination of tachycardia from being too frequent, since such too-frequent terminations may actually interrupt beneficial sinus tachycardia. Consequently, tachycardia which happens to be of sinus origin is not interrupted during the disable interval 47, in contrast to more frequent interruptions in sinus tachycardia if a disable interval were not used.

Figure 4:
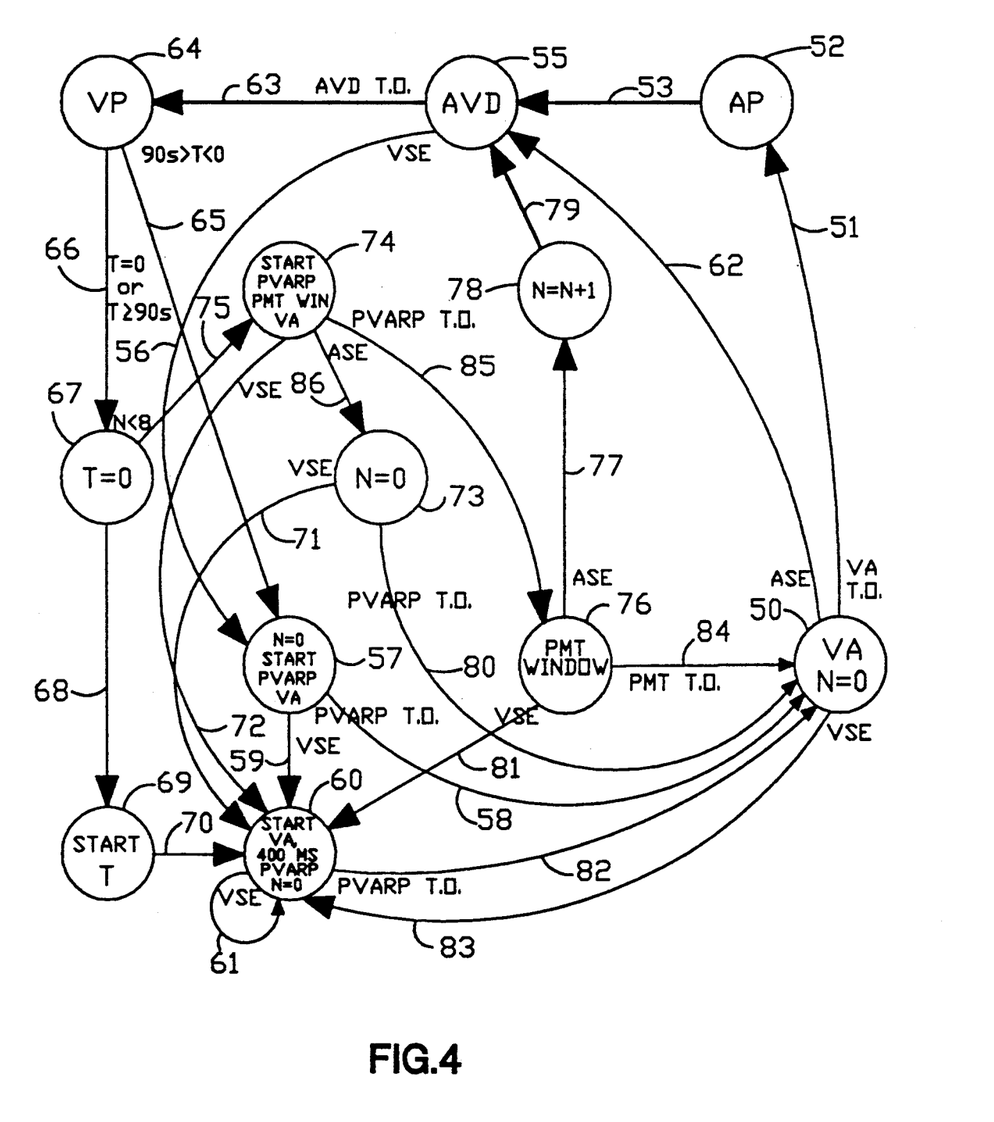
FIG. 4 is a state diagram of the logic of a DDD/DDDR pacer incorporating the invention.

FIG. 4 is a state machine description of a DDD/DDDR activity controlled pacer which incorporates the invention and depicts the operation of logic 20.

Consideration of operation may begin with VA state 50, which corresponds to the atrial observation time of the pacer. In this state the pacer is timing out a VA interval. If the VA timer, times out, the pacer logic moves to the atrial pacing state via state transition 51. In state 52 the pacer delivers an atrial pacing stimulus and moves to the AV delay state 55 via state transition 53. In the AV delay state 55 the pacer times out the programmed AV delay time. If a ventricular sensed event occurs, the pacer logic moves via transition 56 to state 57 where the retrograde event counter is reset to zero and the PPVARP and VA intervals are started. If no ventricular sensed event occurs the pacer moves to the ventricular pacing state 64 via state transition 63. In the ventricular pacing state the pacer delivers a ventricular pacing stimulus to the patient's heart. While in the state 64 the pacer tests the disable timer. If the disable timer is not active or is beyond the selected disable period ($T=0$ or, $T \geq 90$ seconds) then the pacer moves via state transition 66 to state 67 where the retrograde sensed event counter is tested. If the retrograde sensed event counter is full ($N=8$) then the pacer logic moves via state transition 68 to state 69 where the disable timer is started. Next the pacer moves via state transition 70 to state 60 where the extended PVARP is invoked, the retrograde sense counter is reset to zero ($n=0$) and the VA timers are started. If a ventricular sensed event 61 occurs during the extended PVARP, the extended PVARP is restarted. After the PPVARP atrial refractory period of 400 milliseconds is timed out the pacer returns to the VA state 50 via state transition 82.

Alternatively, while in state 50 prior to the VA interval timeout, if an atrial sensed event occurs then the pacer logic moves to the AV delay state 55 via state transition 62. The pacer logic then follows the operation as described herein above. While in state 50 prior to VA interval timeout, if a ventricular sensed event occurs then the pacer logic moves to state 60 via transition 83 whereby the extended PVARP is invoked, the retrograde sense counter is reset to zero ($N=0$), and the VA timer is started. The pacer logic then follows the operation as described above.

Returning consideration to state 67, if the retrograde sensed event counter is not "full" the pacer moves to the state 74 via state transition 75 where the PPVARP is started. When the PPVARP timer times out the pacer moves via state transition 85 to the PMT window state 76 where the retrograde sense window is started. An atrial sensed event occurring while in this state causes state transition 77 to state 78 where the retrograde sensed event counter is incremented by one count. Incrementing the count passes the machine to the AV delay state 55, previously discussed, via state transition 79. While in state 76 if no atrial sensed event occurs the window times out, returning the pacer to state 50 via state transition 84.

Returning to the PMT window state 76, if a ventricular sensed event occurs, the pacer logic moves to state 60 via transition 81 whereby the extended PVARP is invoked, the retrograde sense counter is reset to zero ($N=0$) and the VA timer is started. The pacer logic then follows the operation as described above.

During state 74, the occurrence of an atrial sensed event during the PMT sense window causes the pacer to enter state 73 via state transition 86 which resets the retrograde sensed event counter to zero in state 73. The occurrence of a ventricular sensed event during the PMT sense window in state 76 causes the pacer logic to enter state 60 via state transition 72 whereby the extended PVARP is invoked, the retrograde sense counter is reset to zero ($N=0$) and the VA timers are started. The occurrence of a ventricular sensed event during the PPVARP while in state 73 moves the pacer to state 60 via state transition 71. If no ventricular sensed event occurs during the remainder of the PPVARP, the pacer moves to state 50 via state transition 80.

Entry into state 57 via state transition 65 indicates that the disable counter has not expired. Therefore the PPVARP value is used for the refractory duration and the retrograde event counter may be reset to zero within state 57. When this programmed refractory period expires the pacer moves to state 50 via state transition 58. If, however, a ventricular sensed event occurs during state 57 the pacer moves to state 60 via state transition 59 and the VA time intervals are started.

Variations and modifications to the present invention may be possible given the above disclosure. However, all such variations and modifications are intended to be within the scope of the invention claimed by this letters patent.

I claim:

1. A pacer for pacing a patient's heart comprising:
   atrial sensing means for generating an atrial sensed event in response to a depolarization of atrial tissue;
   AV delay timer means for defining an AV delay interval, said AV delay timer means coupled to said atrial sensing means, said AV delay interval initiated by the occurrence of an atrial sensed event;
   ventricular pace stimulator means coupled to said AV delay timer means for generating a ventricular pacing stimulus at the conclusion of said AV delay interval;
   post ventricular atrial refractory period (PVARP) means coupled to said ventricular pacing stimulator means for defining a first predefined post ventricular atrial refractory period extending for a first predefined interval after the generation of said ventricular pacing stimulus;
   retrograde sense window timing means for defining a retrograde sense window after said PVARP;
   retrograde sensed event counter means for counting atrial sensed events occurring during retrograde sense windows defining a retrograde sense count;
   post ventricular atrial refractory period extension means for defining an extended PVARP in response to a predetermined count of said retrograde sensed event counter means, said extended PVARP including said first predefined interval plus an extension;
   retrograde sense window disable means for defining a disable time interval during which possible extended PVARPs are inhibited, said retrograde sense window disable means coupled to said retrograde sense counter means and invoked immediately following an initiation of an extended PVARP when said counter means reaches said predetermined count of said retrograde sensed event counter; and
   means for resetting said retrograde sense count after said predetermined count has been reached.

2. The pacer in claim 1 wherein said retrograde sensed event counter means sets said predetermined count equal to 10 or less.

3. The pacer in claim 1 wherein said retrograde sensed event counter means sets said predetermined count equal 8.

4. The pacer in claim 3 wherein said retrograde sense window disable means sets said disable time interval substantially equal to 90 seconds.

5. The pacer in claim 4 wherein said post ventricular atrial refractory period extension means sets said extended PVARP substantially equal to 400 milliseconds.

6. The pacer in claim 1 wherein said retrograde sense window disable means sets said disable time interval substantially equal to 90 seconds.

7. The pacer in claim 1 wherein said post ventricular atrial refractory period extension means sets said extended PVARP substantially equal to 400 milliseconds.

8. A pacing method for pacing a patient's heart with a pacer comprising:
   detecting atrial sensed events;
   defining an AV delay interval, said AV delay interval initiated by an atrial sensed event;
   generating a ventricular pacing stimulus after said AV delay interval;
   predefining a first post ventricular atrial refractory period (PVARP) extending for a first predetermined interval after the generation of said ventricular pacing stimulus;
   defining a retrograde sense window which begins after said PVARP;
   counting atrial sensed events occurring during retrograde sense windows and defining a retrograde sense count in response thereto, to be stored in a retrograde sensed event counter;
   defining a disable time interval which is invoked immediately following an initiation of an extended PVARP when said retrograde sense count reaches a predetermined value;
   defining an extended PVARP in response to a count of said retrograde sensed event counter, said extended PVARP including said first predefined interval plus an extension, and said extended PVARP being inhibited during said disable interval; and
   resetting said retrograde sense counter after said predetermined value has been reached.

9. The pacing method in claim 8 further comprising setting said predetermined value to a number less than or equal to 10.

10. The pacing method in claim 8 further comprising setting said predetermined value equal to 8.

11. The pacing method in claim 10 further the comprising setting said disable time interval substantially equal to 90 seconds.

12. The pacing method in claim 11 further comprising setting said extended PVARP substantially equal to 400 milliseconds.

13. The pacing method in claim 8 further comprising setting said disable time interval substantially equal to 90 seconds.

14. The pacing method in claim 8 further comprising setting said extended PVARP substantially equal to 400

15. The pacing method in claim 8 further comprising determining whether said atrial sensed events are refractory, and wherein said resetting step comprises resetting said retrograde sensed event counter after said predetermined value has been reached, and after a non-refractory atrial sensed event.

16. The pacing method in claim 8 wherein said resetting step comprises resetting said retrograde sensed event counter after said predetermined value has been reached, and after an atrial paced event.

17. The pacing method in claim 8 further comprising detecting ventricular sensed events, and wherein said resetting step comprises resetting said retrograde sensed event counter after said predetermined value has been reached, and after a ventricular sensed event.

* * * * *

UNITED STATES PATENT AND TRADEMARK OFFICE
CERTIFICATE OF CORRECTION

PATENT NO. : 5,312,450
DATED : May 17, 1994
INVENTOR(S) : H. Toby Markowitz

It is certified that error appears in the above-indentified patent and that said Letters Patent is hereby corrected as shown below:

Column 5, Line 50, delete "Rewave", and insert in its place --R-wave--.

Column 8, Line 52, delete "counter;", and insert in its place --counter means;--.

Column 9, Lines 15-16, delete "predetermined", and insert in its place --predefined--.

Signed and Sealed this

Twentieth Day of September, 1994

Attest:

BRUCE LEHMAN

Attesting Officer     Commissioner of Patents and Trademarks